US012599633B2

(12) United States Patent
Lundgren Åkerlund et al.

(10) Patent No.: US 12,599,633 B2
(45) Date of Patent: Apr. 14, 2026

(54) MESENCHYMAL STEM CELLS FOR USE IN THE TREATMENT OF SKIN DEFECTS

(71) Applicant: Xintela AB, Lund (SE)

(72) Inventors: Evy Lundgren Åkerlund, Bjärred (SE); Folke Sjöberg, Linköping (SE); Hooi Ching Lim, Lund (SE); Ahmed Elserafy, Linköping (SE); Moustafa Elmasry, Linköping (SE)

(73) Assignee: Xintela AB, Lund (SE)

( * ) Notice: Subject to any disclaimer, the term of this patent is extended or adjusted under 35 U.S.C. 154(b) by 413 days.

(21) Appl. No.: 18/560,712

(22) PCT Filed: May 20, 2022

(86) PCT No.: PCT/EP2022/063731
§ 371 (c)(1),
(2) Date: Nov. 14, 2023

(87) PCT Pub. No.: WO2022/243517
PCT Pub. Date: Nov. 24, 2022

(65) Prior Publication Data
US 2024/0245726 A1      Jul. 25, 2024

(30) Foreign Application Priority Data
May 20, 2021      (EP) .................................... 21174929

(51) Int. Cl.
| | |
|---|---|
| A61K 35/28 | (2015.01) |
| A61K 47/42 | (2017.01) |
| A61P 17/02 | (2006.01) |

(52) U.S. Cl.
CPC .............. A61K 35/28 (2013.01); A61K 47/42 (2013.01); A61P 17/02 (2018.01)

(58) Field of Classification Search
CPC ....... A61K 35/28; A61K 9/0014; A61P 17/02; A61L 2430/34
See application file for complete search history.

(56) References Cited

U.S. PATENT DOCUMENTS

2009/0232777 A1      9/2009  Lundgren-Akerlund et al.

FOREIGN PATENT DOCUMENTS

| | | | | |
|---|---|---|---|---|
| WO | WO-03106492 A1 | * | 12/2003 | ........... C12N 5/0663 |
| WO | WO 2018/138322 A1 | | 8/2018 | |

OTHER PUBLICATIONS

Yolanda et. al.: Adult Stem Cell Therapy in Chronic Wound Healing, J. Stem Cell Res Ther., vol. 4:1, 2014.
Dominici M. et al.: Minimal criteria for defining multipotent mesenchymal stromal cells, Cytotherapy, vol. 8, No. 4: 315-317, 2006.

El-Serafi Ahmed T. et al.: Cell Therapy, the Future Trend for Burn Management, Editorial in Clinics in Surgery 3:1896, 2018.
El-Serafi Ahmed T. et al.: Skin regeneration in three dimensions, current status, challenges and opportunities; Differentiation 96: 26-29, 2017.
Garcia-Bernal D. et al.: The Current Status of Mesenchymal Stromal Cell: Controversies, Unresolved Issues and Some Promising Solutions to Improve Their Therapeutic Efficiacy, Front. in Cell and Dev. Biol. vol. 9, Mar. 2021.
Guillamat-Prats R.: The Role of MSC in Wound Healing, Scarring and Regeneration, Cells, 2021, 10(7).
Jackson Wesley M. et al.: Concise review: clinical translation of wound healing therapies based on mesenchymal stem cells; Stem Cells Translational Medicine, vol. 1, 2012, pp. 44-50.
Jeschke M.G. et al.: A surgical device to study the efficacy of bioengineered skin substitutes in mice wound healing models, Tissue Eng: Part C, 2017, 23(4):237-42.
Karlsson M. et al.: Sprayed cultured autologous keratinocytes in the treatment of severe burns: A retrospective matched cohort study, Annals of Burns and Fire Disasters, vol. 33(2); Jun. 2020.
Kosaric Nina et al.: Stem cell therapies for wound healing, Expert Opinion on Biological Therapy, 19:6, 575-585, 2019.
Otero-Viñas Marta et al.: Mesenchymal Stem Cells in Chronic Wounds: The Spectrum from Basic to Advance Therapy, Advances in Wound Care, vol. 5, No. 4, 2016, pp. 149-163.
Raghuram Anjali C. et al.: Role of stem cell therapies in treating chronic wounds: A systematic review; vol. 12, No. 7, Jul. 2020, pp. 659-675.
Smith A. N. et al.: Mesenchymal stem cells induce dermal fibroblast responses to injury, Experimental Cell Research, 316, 2010, pp. 48-54.
Sullivan T.P. et al.: The pig as a model for human wound healing, Wound Repair Regen. 2001; 9(2):66-76.
Tamai Katsuto et al.: Stem Cell Therapy for Epidermolysis Bullosa-Does It Work?; Journal of Investigative Dermatology, vol. 136, No. 11, 2016, pp. 2119-2121.
Uvebrant K. et al.: Integrin a10B1-selected Equine MSCs have Improved Chondrogenic Differentiation, Immunomodulatory and Cartilage Adhesion Capacity, Annals of Stem Cell Research, vol. 1, Issue 1, 2018.

(Continued)

*Primary Examiner* — Jeremy C Flinders
*Assistant Examiner* — Masudur Rahman
(74) *Attorney, Agent, or Firm* — Weston R. Gould; Dinsmore & Shohl LLP

(57) ABSTRACT

The present invention relates to therapeutics and methods for treating skin defects using compositions comprising integrin a10-selected Mesenchymal Stem Cells (MSCs) Disclosed herein are integrin α10-selected MSC populations and culture conditions that enhance cell viability, paracrine activity, and regenerative function when administered to damaged skin tissue. The compositions promote wound healing, modulate inflammatory responses, and support re-epithelialization. Further disclosed herein are dosing parameters and administration routes suitable for improving healing outcomes in acute and chronic skin defects.

20 Claims, 7 Drawing Sheets

(56) References Cited

OTHER PUBLICATIONS

Wu Yan et al.: Bone marrow-derived mesenchymal stem cell attenuates skin fibrosis development in mice, International Wound Journal, vol. 11, 2014, pp. 701-710.

* cited by examiner

A

B
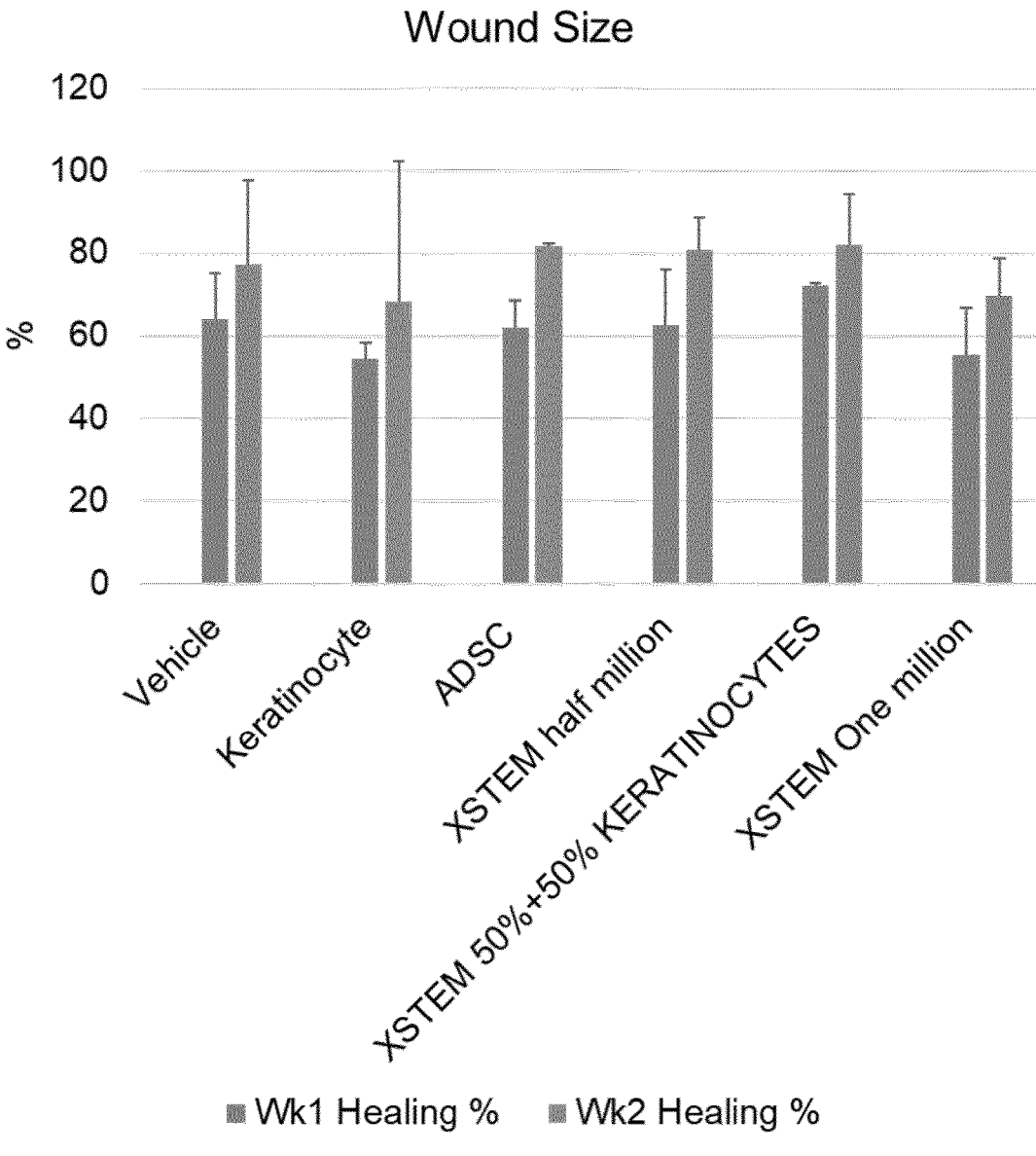
Fig. 4 – cont.

A

B

C
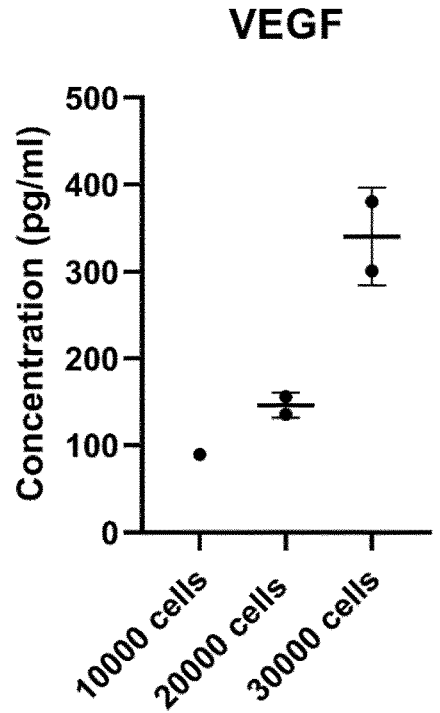
D
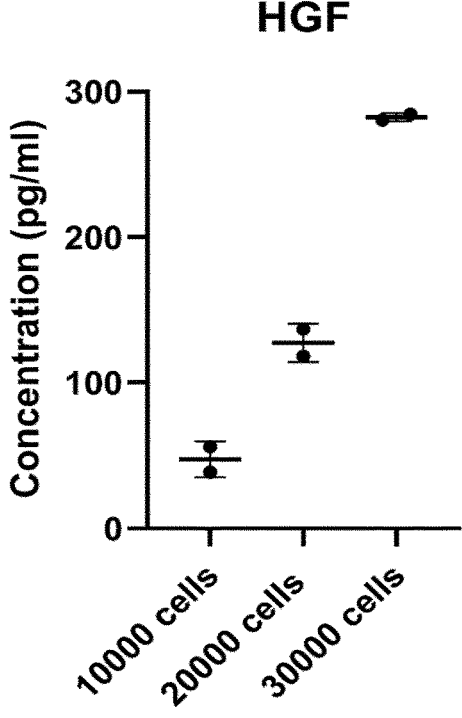
Fig. 5 - cont.

MESENCHYMAL STEM CELLS FOR USE IN THE TREATMENT OF SKIN DEFECTS

CROSS-REFERENCE TO RELATED APPLICATIONS

This application is a national phase entry pursuant to 35 U.S.C. § 371 of International Application No. PCT/EP2022/063731, filed May 20, 2022, which claims the benefit of priority to EP Application Serial No. 21174929.6, filed May 20, 2021, each of which is incorporated by reference herein in its entirety for any purpose.

TECHNICAL FIELD

The present invention relates to compositions comprising integrin α10-selected Mesenchymal Stem Cells (MSCs) for use in the treatment of skin defects.

BACKGROUND

Chronic skin wounds are considered to be a huge challenge for the health care systems. The incidence of chronic ulcers as a consequence of diabetes, vascular insufficiency and pressure sores is rising in correspondence to increasing mean of age. Leg ulcers are estimated to cost the EU total health care about 1-2% of its budget. In United Kingdom, the costs related to pressure ulcers are about 4% of the total health care budget. In addition, difficult-to-heal wounds can be associated with pain, limited mobility, reduced quality of life, limited productivity and financial stresses that can remain for several months or years. On the other hand, burn victims can suffer from life threatening injuries as well as long term consequences. The current management policies are associated with marked decrease in mortality rate, although a corresponding improvement in the functional or aesthetic outcomes for extensive burns >50-60% of the total body surface area has not been achieved, yet.

Cell therapy is an emerging new approach to improve wound healing and coverage of large burn wounds with or without being combined with meshed autologous skin grafts, to replace damaged skin and enhance regeneration (El-Serafi et al. 2017; El-Serafi et al. 2018). Cultured autologous keratinocytes were investigated as an advanced therapeutic medicinal product. Unfortunately, many challenges were encountered, such as the difficulty to isolate, slow proliferation rate and the need of a skin biopsy to isolate the cells, which may not be accessible in severe cases (Karlsson et al. 2020). Furthermore, the epidermal layer formed by these cells is usually fragile due to limited flexibility. As an alternative and potential source, adipose derived stem cells (ADSC) pose the potential to differentiate into various cell lineages, including the epidermal cells (Kosaric et al. 2019; Raghuram et al. 2020). Unfortunately, the efficient in vitro differentiation of ADSC into epidermal cells represents an unmet challenge. On the other hand, the local application of ADSC and other stem cell types can be associated with enhanced healing properties.

MSCs were used for the first time as cellular pharmaceutical agents in humans in 1995. After several years utilizing MSCs as therapeutical agents, numerous questions on their behaviour remain unsolved, including the heterogeneity of the MSC populations in the final product, the adequate conditions to activate in vivo their immunomodulatory capabilities, the consequences of the banking procedures, the best route for their delivery, their response to stressful conditions (Garcia-Bernal et al. 2021).

SUMMARY

The present invention is directed to a composition comprising integrin alpha 10-selected Mesenchymal Stem Cells (MSCs), thus a homogeneous composition of MSCs, for use in treatment and/or regeneration of a skin defect in a mammal. In fact, the present inventors have found that integrin alpha 10-selected MSCs, also referred to as XSTEM herein, locally applied on a wound results in excellent healing of wounds in a pig model and that the newly formed skin tissue closely resembles normal skin. Regeneration of the basal membrane, keratinization of the skin and formation of high level of collagen structured in bundles and resembling the naturally occurring collagen in skin was shown. Integrin alpha 10-selected MSCs also showed less scarring compared to transplanted skin cells. Most interestingly, integrin alpha 10-selected MSCs produces a more robust and complete reepithelization compared to other cells tested, including autologous keratinocytes or stem cells, the latter being a heterogeneous cell composition comprising also MSCs which have not being selected for a specific marker, and in particular which have not being selected for integrin alpha 10 expression.

Selecting MSCs based on the expression of integrin alpha 10 on their surface results in the production of a homogeneous cell composition having superior immunomodulatory, anti-inflammatory and skin regenerative capabilities compared to cell composition comprising non-selected MSCs.

In one aspect of the present disclosure it is provided a composition comprising integrin alpha 10-selected Mesenchymal Stem Cells (MSCs) for use in treatment and/or regeneration of a skin defect in a mammal.

In another aspect of the present disclosure it is provided a use of a cosmetic composition comprising integrin alpha 10-selected Mesenchymal Stem Cells (MSCs) for reducing scar formation resulting from healing of a skin defect in a mammal.

In another aspect of the present disclosure it is provided a use of a composition comprising integrin alpha 10-selected Mesenchymal Stem Cells (MSCs) for non-therapeutic treatment of a skin defect in a mammal.

DEFINITIONS

Figure 1:
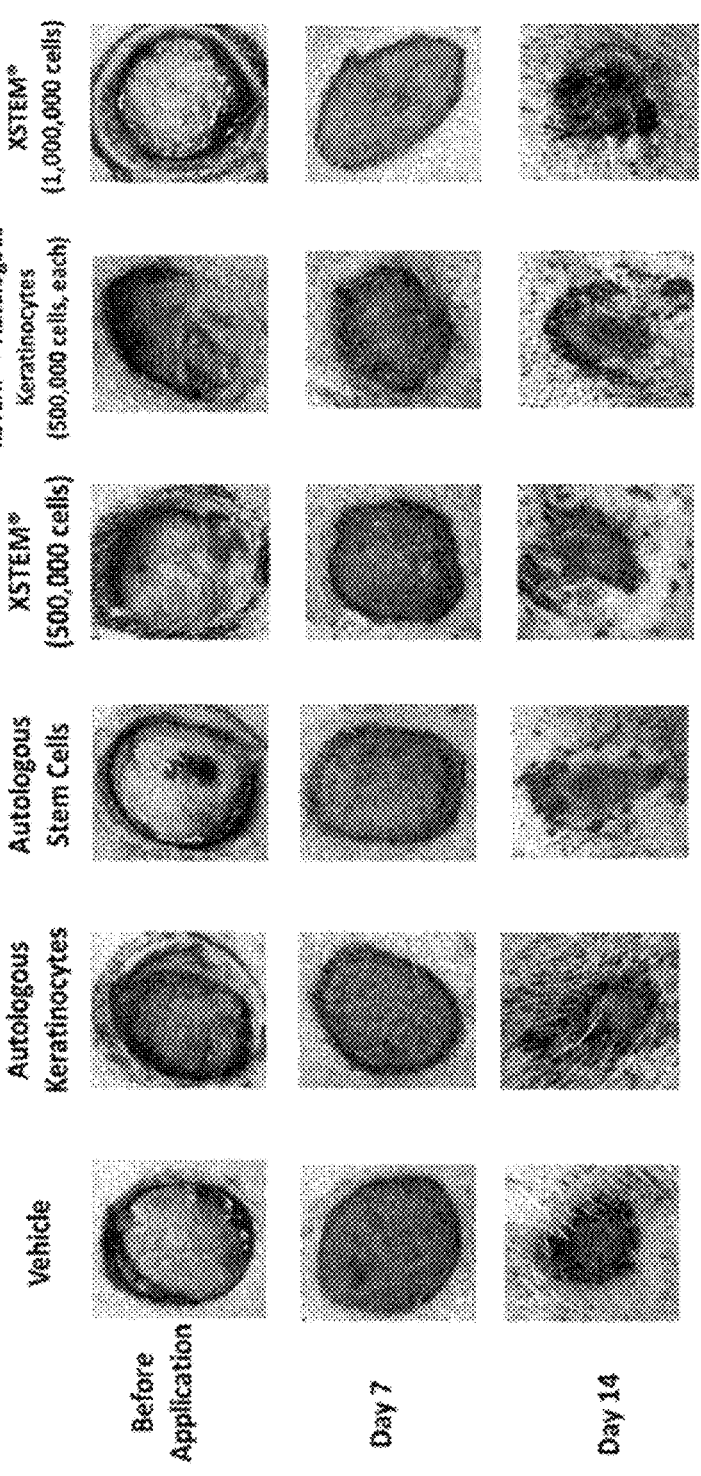
FIG. 1: Macroscopic images of the wounds immediately after creating the surgical wounds; i.e. before cell application, as well as after one and two weeks. No signs of inflammation, laceration or infection could be detected at any of the wounds. The wound healing pattern of autologous stem cells (half a million) and XSTEM at half million cells with and without autologous keratinocytes was of particular interest. The vehicle was 2.5% human serum albumin in saline.

"Anti-integrin α10 antibody" or "anti-integrin α10 subunit antibody" is used herein interchangeably to refer to an antibody capable of recognizing and binding to at least the integrin α10 subunit of the heterodimeric protein integrin α10β1. These antibodies may be antibodies that recognize an epitope of the heterodimeric protein integrin α10β1, wherein the epitope comprises amino acid residues of both the integrin α10 and the integrin β1 subunit.

"Integrin α10" or "integrin alpha10" as used herein refers to the α10 subunit of the heterodimeric protein integrin α10β1. This denotation does not exclude the presence of the integrin β1 subunit bound to the integrin α10 subunit thus forming the quaternary structure of integrin α10β1 heterodimer. The human integrin α10 chain sequence is known and publicly available at GenBank™/EBI Data Bank accession number AF074015 and has been described in (Camper 1998). "Alpha" and "α", as well as "alpha10" and "alpha 10" are equivalent terms.

As used herein, the singular forms "a", "an" and "the" include plural referents unless the context clearly states otherwise.

The term "some embodiments" can include one, or more than one embodiment.

The use of the word "a" or "an" when used throughout the text or in conjunction with the term "comprising" in the claims and/or the specification may mean "one," but it is also consistent with the meaning of "one or more," "at least one," and "one or more than one."

The terms "isolating", "sorting" and "selecting" as used herein refer to the action of identifying a cell as being a certain type of cell and separating it from cells that do not belong to the same cell type or to another differentiation state. Further, these terms may also refer to the action of identifying a cell by the presence of a certain marker. For example, in the present invention in directed to integrin alpha 10-selected Mesenchymal Stem Cells (MSCs). Usually, isolation refers to a first step of separation, which may for example be mechanical, whereas "selection" is more specific and for example performed with the help of an antibody. The person skilled in the art will understand that the procedure of "isolating", "sorting" or "selecting" cells leads to an enrichment of said cells.

The term "integrin alpha 10-enriched MSCs" as used herein is synonymous to the terms "integrin alpha $10^{high}$ MSCs", "integrin alpha 10-selected mesenchymal stem cells" and "an enriched integrin $\alpha 10^{high}$ population of mesenchymal stem cells". As described in Example 1, the MSCs used in the invention are selected using procedures to enrich MSCs expressing integrin alpha10, for example by selecting those MSCs which express integrin alpha 10 with the help of an anti-integrin alpha 10 antibody. The person skilled in the art will understand that cells selected for specific properties, e.g. MSCs expressing integrin alpha10, or integrin alpha $10^{high}$ MSCs, may form a specific, homogeneous cell population.

"Mesenchymal stem cells" or "MSCs" as used herein refers to multipotent stromal cells as defined by The Mesenchymal and Tissue Stem Cell Committee of the International Society for Cellular Therapy (see Dominici M et al., Cytotherapy. 8(4):315-7 (2006)). MSCs must be plastic-adherent when maintained in standard culture conditions, and must express CD105, CD73 and CD90, and lack expression of CD45, CD34, CD14 or CD11b, CD79alpha or CD19 and HLA-DR surface molecules. MSCs must have the capacity to differentiate to osteoblasts, adipocytes or chondroblasts in vitro.

As used herein, the term "skin defect" refers to, but is not limited to: injuries or trauma to internal or external tissue, preferably injury or trauma to the epidermis and/or dermis of the skin. The wound may be an acute wound or a chronic wound. By way of example, an acute wound may be an incision, laceration, abrasion graze or burn, a puncture wound, a penetration wound or a wound due to dermatologic diseases such as psoriasis, acne and eczema. By way of example, a chronic wound may be a venous ulcer, a diabetic ulcer, a pressure ulcer, corneal ulcer, digestive ulcer or wounds as a result of ischemia and radiation poisoning.

As used herein "treatment and/or regeneration of a skin defect" relates to the promotion, the acceleration, and/or the improvement of healing at the wounded site, i.e. the formation of a functional skin at the wounded site. As such "treatment and/or regeneration of a skin defect" ideally result in formation or regeneration of dermis and epidermis, including a basal layer, which characterize functional skin.

The terms "hard-to-heal wound", "difficult-to-heal wound" and "chronic wound" are used herein interchangeably. The terms "hard-to-heal wound" and "chronic wound" as used herein refer to a wound that has not healed. Wounds that do not heal within approximately 4 to 6 weeks, for example, are considered chronic. A "chronic wound" may be a wound that fails to progress through an orderly and timely sequence of repair or a wound that does not respond to treatment and/or the demands of treatment are beyond the patient's physical health, tolerance or stamina. Many wounds that are first considered to be acute wounds ultimately become chronic wounds due to factors still not well understood. One significant factor is the transition of planktonic bacteria within the wound to form a biofilm. For example, a chronic wound may have an epithelial layer that fails to cover the entire surface of the wound and is subject to bacterial colonization, which can result in biofilm formation, which is resistant to treatment with anti-bacterial agents.

Commonly, chronic wounds are classified into three broad categories based on their main cause: venous insufficiency, arterial insufficiency and diabetic complications, or is a pressure-related. Hard-to-heal wounds due to venous insufficiency account for 70% to 90% of all hard-to-heal wounds and commonly affect the elderly. Venous insufficiency results in venous hypertension, in which blood flow is abrogated resulting in subsequent ischaemia. Venous insufficiency can occur as a result of obstructions to venous outflow or reflux due to valve damage. Following a period of ischaemia, tissue reperfusion can result in reperfusion injury, causing the tissue damage that leads to wound formation.

Exemplary chronic wounds can include "burn ulcers", including first degree burn, which may be a superficial, reddened area of skin; second degree burn, which may be a blistered injury site which may heal spontaneously after the blister fluid has been removed; third degree burn, which may be a burn through the entire skin and usually require surgical intervention for wound healing; scalding burns, which may occur from scalding hot water, grease or radiator fluid; thermal burns, which may occur after contact with flames, usually deep burns; chemical burns, which may come from acid and alkali, usually deep burns; electrical burns; and contact burns, which are usually deep and may occur from muffler tail pipes, hot irons and stoves, or other materials.

The terms "severe inherited blistering disease" and "epidermolysis bullosa" are used herein interchangeably.

"Preventing" or "Prevention" as used herein, includes delaying, stopping, reducing the risk of the onset, of disease, disorder, or condition.

DETAILED DESCRIPTION

Integrin Alpha 10-Selected Mesenchymal Stem Cells

In some embodiments of the present disclosure, at least 50% of the MSCs express integrin α10 subunit.

Example 1 describes a way of manufacturing the integrin alpha 10 selected MSCs presented in the present disclosure. The key advantage of the integrin alpha 10 selected MSCs is that they have been selected using the criteria of integrin alpha 10 protein expression and are thus a homogeneous culture and/or population of MSCs. These cells have been shown to exhibit robust expression of stem cell markers, see for example WO 2018/138322. The skilled person in the art will know that several methods for selecting, and thereby enriching cells, can be used. In the present invention, integrin alpha 10 expressing MSCs are enriched during the isolation/selection procedure. For this, an anti-integrin alpha 10 antibody may be used. MSC isolation and selection may be performed as described in WO 2018/138322, incorporated herein by reference. As disclosed in Example 1, at the selection stage the selected MSCs, which are selected by their expression of integrin alpha 10 using an anti-integrin alpha 10 antibody, express integrin alpha10. More specifically, the selected cells are MSCs which express the heterodimer integrin alpha 10 beta1(α10β1), since the integrin alpha 10 subunit is expressed together with the integrin beta1 subunit. The selection stage is followed by an expansion stage where integrin alpha 10 expression of each of the selected MSCs may vary, i.e. not all MSCs may express integrin alpha 10 at all time during expansion and thus at the time of administration. However, at the time of administering the MSCs to a patient, at least 50% of the administered cells express integrin alpha 10 subunit.

In some embodiments of the present disclosure, at least 50%, such as at least 55%, such as at least 60%, such as at least 65%, such as at least 70%, such as at least 75%, such as at least 80%, such as at least 85%, such as at least 90%, such as at least 95%, such as at least 96%, such as at least 97%, such as at least 98%, such as at least 99%, such as at least 100% of the MSCs express integrin alpha 10 subunit.

In some embodiments of the present disclosure, the MSCs are MHC class II, CD45, CD34, CD11b and/or CD19 negative.

In some embodiments of the present disclosure, the MSCs express CD73, CD90 and/or CD105.

In some embodiments of the present disclosure, the composition secretes growth factors, anti-inflammatory factors and/or immunomodulatory factors.

In some embodiments of the present disclosure, the composition secretes growth factors, anti-inflammatory factors and/or immunomodulatory factors at higher concentration compared to a composition wherein less than 50% of the MSC express integrin alpha 10 subunit.

In some embodiments of the present disclosure, the composition secretes growth factors, anti-inflammatory factors and/or immunomodulatory factors at higher concentration compared to a composition wherein less than 50% of the MSC express integrin alpha 10 subunit.

In some embodiments of the present disclosure, the growth factors, anti-inflammatory factors and/or immunomodulatory factors are indoleamine 2,3-dioxygenase (IDO), prostaglandin E2 (PGE2), vascular endothelial growth factor (VEGF) and/or hepatocyte growth factor (HGF). Vascular endothelial growth factor (VEGF) and hepatocyte growth factor (HGF) are growth factors that promote tissue regeneration and skin regeneration. The integrin alpha 10-selected MSCs of the present disclosure, secrete these factors in higher amount and/or concentration compared to MSCs population which have not been selected for integrin alpha 10 expression and are therefore more effective in treating chronic wounds as defined herein and regenerate skin at the site of a skin defect.

In some embodiments of the present disclosure, the MSCs are selected from the group consisting of a mesenchymal stem cells, mesenchymal progenitor cells, and mesenchymal stromal cells; or a mixture thereof.

In some embodiments of the present disclosure, the MSCs are induced to express integrin α10 subunit.

In some embodiments of the present disclosure, the MSCs are cultured in a culture media comprising mammalian serum and FGF-2.

In some embodiments of the present disclosure, the MSCs are cultured in a culture media comprising platelet lysate and/or platelet lysate components.

In some embodiments of the present disclosure, the MSCs are cultured in a culture media comprising FGF-2 and platelet lysate and/or platelet lysate components.

In some embodiments of the present disclosure, the MSCs are cultured in a culture media comprising mammalian serum and platelet lysate and/or platelet lysate components.

In some embodiments of the present disclosure, the MSCs are cultured in a culture media comprising TGFβ.

In some embodiments of the present disclosure, the MSCs are cultured in a culture media comprising FGF2.

In some embodiments of the present disclosure, the MSCs are cultured in a serum-free culture media comprising platelet lysate and/or platelet lysate components.

In some embodiments of the present disclosure, the MSCs are cultured in a serum-free culture media comprising growth factors.

In some embodiments of the present disclosure, the MSCs are cultured in a serum-free culture media comprising the growth factors FGF2 and/or TGFβ.

In some embodiments of the present disclosure, the MSCs are allogeneic or autologous.

In some embodiments of the present disclosure, the MSCs and mammal are from the same species.

In some embodiments of the present disclosure, the MSCs and mammal are from different species.

In some embodiments of the present disclosure, the MSCs are isolated from a mesenchymal stem cell-containing tissue, selected for expression of integrin alpha10beta1, and expanded in culture.

In some embodiments of the present disclosure, the selection of MSCs has been conducted with an anti-integrin α10 antibody.

In some embodiments of the present disclosure, the MSCs are derived from adipose tissue, bone marrow, synovial membrane, peripheral blood, cord blood, umbilical cord blood, Wharton's jelly, and/or amniotic fluid.

In some embodiments of the present disclosure, the MSCs are derived from adipose tissue.

In some embodiments of the present disclosure, the MSCs are derived from bone marrow.

In some embodiments of the present disclosure, the MSCs are derived from fetal, neonatal, juvenile or adult MSCs and/or progenitor cells.

In some embodiments of the present disclosure, the MSCs are not derived from embryonic cells or from an embryo.

In some embodiments of the present disclosure, the MSCs are an in vitro cell culture.

In some embodiments of the present disclosure, the MSCs are an in vitro cell suspension.

In some embodiments of the present disclosure, the composition comprising integrin alpha 10-selected MSCs is a cosmetic composition.

In some embodiments of the present disclosure, the composition comprising integrin alpa10-selected MSCs is a non-therapeutic composition.

Treatment of a Skin Defect

In one aspect, the present disclosure provides a composition comprising integrin alpha 10-selected Mesenchymal Stem Cells (MSCs) for use in treatment and/or regeneration of a skin defect in a mammal.

Another aspect of the present disclosure provides a composition comprising integrin alpha 10-selected Mesenchymal Stem Cells (MSCs) for use in the prevention of fibrosis of the skin in a mammal.

A further aspect of the present disclosure provides a method for regeneration of skin at the site of a skin defect and/or for reducing scar formation resulting from healing of a skin defect in a mammal, said method comprising administering a composition comprising integrin alpha 10-selected Mesenchymal Stem Cells (MSCs) to the skin defect.

The treatment disclosed herein targets a number of skin defects. These may be divided into the following non-extensive list of categories: hard-to-heal wounds or chronic wounds, skin disorders provoked by external factors, inflammatory dermatosis, postprocedural disorders of the skin, and genetic or developmental disorders of the skin, such as hereditary disorders of the skin.

In some embodiments of the present disclosure, it is provided a composition comprising integrin alpha 10-selected MSCs for use in treatment and/or regeneration of a skin defect in a mammal, wherein the skin defect is a hard-to-heal wound, such as a chronic wound.

The present inventors have shown the capabilities of integrin alpha 10-selected MSCs to heal a skin defect, such as a hard-to-heal wound, in a pig model, which is the most accepted and widely used animal model for testing healing of skin defects, including hard-to-heal wounds, of humans. In fact, amongst the animals used for testing, pigs have the skin that resembles human skin the most. Moreover, the wound healing course and process of acute wounds and hard-to-heal wounds is in principle the same, expect for the possible presence of underlying diseases in some cases of hard-to-heal wounds. In addition, the size and depth of full thickness wounds created in our study mimics chronic wounds as the large wound sizes did not allow spontaneous healing via contracture. The person skilled in the art will acknowledge that other animal models may be used to confirm the capabilities of integrin alpha 10-selected MSCs to heal a skin defect.

The integrin alpha 10-selected MSC of the present disclosure are suitable and successful in treating skin defects, including hard to heal wounds, thanks to their demonstrated capability of regenerating skin and secreting factors that promote wound healing by acting against inflammation and by modulating the immune system, and/or by promoting tissue regeneration.

In some embodiments of the present disclosure, the hard-to-heal wound is associated with venous insufficiency, arterial insufficiency and diabetic complications, a rare disease such as sickle cell anaemia or is a pressure-related hard-to-heal wound.

In some embodiments of the present disclosure, the hard-to-heal wound is a dermal ulcer, a wound, or a skin defect due to vascular insufficiency or diabetic affection of the blood vessels. For example, diabetic foot syndrome/diabetic foot ulcers, and diabetic neuropathic ulcer are types of hard-to-heal wounds, which may benefit of the treatment of the present disclosure.

In some embodiments of the present disclosure, the skin defect is a skin disorders provoked by external factors.

Examples of skin disorder provoked by external factors, which may benefit of the treatment of the present disclosure are pressure ulceration, dermatoses provoked by friction or mechanical stress, dermatoses due to foreign bodies, dermatoses provoked or exacerbated by exposure to cold, dermatoses provoked by heat or electricity, dermatoses provoked by light or UV radiation, dermatoses due to ionizing radiation, allergic contact dermatitis, photo-allergic contact dermatitis, irritant contact dermatitis, allergic contact urticarial, protein contact dermatitis, allergic contact sensitisation, phototoxic reactions to skin contact with photoactive agents, cutaneous reactions to venomous or noxious animals.

In some embodiments of the present disclosure, the skin disorder provoked by external factors is a burn, a pressure sore from extended bed rest, a skin defect induced by trauma, or a cut.

In some embodiments of the present disclosure, the skin disorder provoked by external factors is a burn. For example, the burn may be a second degree burn, such as a deep burn or burn injury. A burn may be caused by exposure to cold, heat, electricity, light, UV radiation, ionizing radiation, allergens, chemicals such as acids and bases, and other external agents.

In some embodiments of the present disclosure, the skin defect is an inflammatory dermatosis.

Examples of inflammatory dermatosis, which may benefit of the treatment of the present disclosure are dermatitis, eczema, atopic dermatitis, papulosquamous dermatoses, urticaria, angioedema or other urticarial disorders, inflammatory erythemas and other reactive inflammatory dermatoses, immunobullous diseases of the skin, cutaneous lupus erythematosus, scarring or sclerosing inflammatory dermatoses.

In some embodiments of the present disclosure, the skin defect is a postprocedural disorder of the skin.

Examples of postprocedural disorder of the skin, which may benefit of the treatment of the present disclosure are an unsatisfactory surgical scar of skin, a cutaneous flap necrosis, a myocutaneous flap necrosis, a skin graft failure, a composite graft failure.

In some embodiments of the present disclosure, the postprocedural disorder of the skin is a surgical incision.

In some embodiments of the present disclosure, the skin defect is a genetic and/or developmental disorders affecting the skin.

Examples of genetic and/or developmental disorders affecting the skin, which may benefit of the treatment of the present disclosure are epidermolysis bullosa, or genodermatosis, such as pemphigus genodermatosis.

In some embodiments of the present disclosure, the epidermolysis bullosa is selected from the group consisting of epidermolysis bullosa simplex, junctional epidermolysis bullosa, dystrophic epidermolysis bullosa, recessive dystrophic epidermolysis bullosa, syndromic epidermolysis bullosa and epidermolysis bullosa.

Independently of the underlying cause of the skin defect, the composition comprising integrin alpha 10-selected MSCs of present disclosure can be used to treat or regenerate a skin defect having the physical characteristics described herein.

In some embodiments of the present disclosure, the skin defect is an external defect. Thus, the skin defect may be a defect of dermis and/or epidermis.

Further, the skin defect may extend to the subcutis, also referred to as hypodermis or hypoderm.

In some embodiments of the present disclosure, the skin defect is a defect of dermis and/or epidermis and/or subcutis, In some embodiments of the present disclosure, the skin defect is an open defect.

In some embodiments of the present disclosure, the skin defect is an inflamed wound or ulcer.

In some embodiments of the present disclosure, the skin defect is an acute skin defect.

In some embodiments of the present disclosure, the skin defect is a chronic skin defect. As provided herein, a chronic skin defect is a hard-to-heal skin defect. Acute skin defects may become chronic skin defects if they do not heal under normal circumstances within 4-6 weeks.

In some embodiments of the present disclosure, the skin defect is full thickness skin defect. For example a skin defect affecting both the dermis and the epidermis is considered to be a full thickness skin defect.

In some embodiments of the present disclosure, the skin defect is a partial thickness skin defect. For example a skin defect affecting the epidermis and only part of the dermis is considered to be a partial thickness skin defect.

In some embodiments of the present disclosure, the skin defect has a surface area of at least 0.3 cm×0.3 cm, and at the most covers the whole body of the mammal to be treated. The composition comprising integrin alpha 10-selected MSCs of the present disclosure may be used to treat skin defects of any size.

The person skilled in the art, including the trained physician, will recognize that the skin defect can vary depending on the cause of the wound and complications arising during the healing process. For example, a wound of a size of e.g. as small as 0.3 cm×0.3 cm might pose a challenge and, if not healing satisfactorily, an infection risk to the patient, as is common in patients with diabetic complications. On the other hand, certain conditions may afflict up to 100% of the patients skin area, e.g. in cases of severe burns. The herein described integrin alpha 10-selected MSCs may be used to treat a wound of any size.

In some embodiments of the present disclosure, administration of a composition comprising integrin alpha 10-selected MSCs according to the present disclosure results in increased collagen production at the site of administration. Moreover, the produced collagen seems so arrange itself into bundle-like structures which are typical of functional skin.

In some embodiments of the present disclosure, administration of a composition comprising integrin alpha 10-selected MSCs according to the present disclosure results in regeneration of a basal membrane at the site of administration.

In some embodiments of the present disclosure, administration of a composition comprising integrin alpha 10-selected MSCs according to the present disclosure results in keratinization of the skin at the site of administration.

Administration Form

The composition comprising integrin alpha 10-selected Mesenchymal Stem Cells (MSCs) for use in treatment and/or regeneration of a skin defect in a mammal, is, in some embodiments, adapted for local administration.

As used herein "local administration" or "locally administering" means direct administration of a pharmaceutical at, or to the vicinity of, a site on or within an animal body, at which site a biological effect of the pharmaceutical is desired.

In some embodiments of the present disclosure, the composition is topically administered to the skin defect.

In some embodiments of the present disclosure, the composition disclosed herein may be administered via injection. For example, the skin defect may be covered with a film, such as a propylene film or a film made of any other material suitable for covering a skin defect on a mammal, and an enclosure between the skin defect and the film may be formed. Then, the composition disclosed herein may be injected to the skin defect, such as in the enclosure between the skin defect and the film, by letting the injection needle go laterally through the skin. Such procedure is known the person of skill in the art.

In some embodiments of the present disclosure, the composition disclosed herein is administered via injection into the skin.

In some embodiments of the present disclosure, the composition disclosed herein is administered via injection under the skin.

In some embodiments of the present disclosure, the skin defect is covered prior to being treated with the composition disclosed herein.

In some embodiments of the present disclosure, the skin defect is covered after being treated with the composition disclosed herein.

The composition for use according to any one of the preceding items, wherein the composition comprises between 100.000 and 2.000.000 MSCs, such as between 200.000 and 1.000.000 MSCs, such as about 200.000 MSCs, such as about 300.000 MSCs, such as about 400.000 MSCs, such as about 500.000 MSCs, such as about 600.000 MSCs, such as about 700.000 MSCs, such as about 800.000 MSCs, such as about 900.000 MSCs, such as about 1.000.000 MSCs, such as about 1.200.000 MSCs, such as about 1.500.000 MSCs.

Depending on the size of the skin defect to be treated, a different amount of MSCs of the present disclosure may be administered.

In some embodiments of the present disclosure, the composition is dosed to comprise between 20.000 and 150.000 MSCs/cm$^2$ of skin defect to be treated, such as between 30.000 and 130.000 MSCs/cm$^2$ of skin defect to be treated, such as between 30.000 and 120.000 MSCs/cm$^2$ of skin defect to be treated, such as between 30.000 and 100.000 MSCs/cm$^2$ of skin defect to be treated, such as between 30.000 and 90.000 MSCs/cm$^2$ of skin defect to be treated, such as between 30.000 and 80.000 MSCs/cm$^2$ of skin defect to be treated, such as between 30.000 and 75.000 MSCs/cm$^2$ of skin defect to be treated, such as between 30.000 and 70.000 MSCs/cm$^2$ of skin defect to be treated, such as between 30.000 and 60.000 MSCs/cm$^2$ of skin defect to be treated, such as between 40.000 and 60.000 MSCs/cm$^2$ of skin defect to be treated, such as between 40.000 and 70.000 MSCs/cm$^2$ of skin defect to be treated, such as between 40.000 and 75.000 MSCs/cm$^2$ of skin defect to be treated, such as between 40.000 and 80.000 MSCs/cm$^2$ of skin defect to be treated, such as between 50.000 and 100.000 MSCs/cm$^2$ of skin defect to be treated, such as between 50.000 and 120.000 MSCs/cm$^2$ of skin defect to be treated, such as between 50.000 and 130.000 MSCs/cm$^2$ of skin defect to be treated, such as between 50.000 and 150.000 MSCs/cm$^2$ of skin defect to be treated.

In some embodiments of the present disclosure, the composition is administered in a form of a cell suspension in a pharmaceutically acceptable liquid medium.

In some embodiments of the present disclosure, the pharmaceutically acceptable liquid medium comprises human serum albumin.

In some embodiments of the present disclosure, the pharmaceutically acceptable liquid medium comprises human serum albumin, such as clinical grade human serum albumin, diluted in saline.

In some embodiments of the present disclosure, the composition is administered in a form of a cell suspension in 2.5% clinical grade human serum albumin diluted in saline.

Alternatively, or in addition, to locally administering the MSCs or composition of the present disclosure by injection, it is also possible to treat the skin defect by using a dressing or reservoir, which have been loaded with the integrin alpha 10-selected MSCs. Thus, in some embodiments of the present disclosure, the composition is administered topically to the skin defect on a dressing or reservoir.

In some embodiments of the present disclosure, the MSCs four use in treatment and/or regeneration of a skin defect are allogeneic.

In some embodiments of the present disclosure, the MSCs four use in treatment and/or regeneration of a skin defect are autologous.

In some embodiments of the present disclosure, the composition further comprises a hydrogel. A hydrogel may help in protecting the site of the skin defect from infection and may therefore help the healing process.

Various hydrogels known to the person of skill in the art for their use in moisturizing skin may be used. For example, the hydrogel may be fibrin glue, hyaluronic acid, gelatin, collagen, alginic acid, cellulose or pectin, or any functionally equivalent hydrogel.

In some embodiments of the present disclosure, the composition further comprises keratinocytes, such as autologous or allogenic keratinocytes. Keratinocytes may help in promoting epithelialisation and restoration of the vascular network on the site of the skin defect.

In some embodiments of the present disclosure, the composition further comprises an anti-inflammatory agent. Presence of an anti-inflammatory agent may help in minimizing inflammation on the site of the skin defect, which in turns may help in promoting healing.

In some embodiments of the present disclosure, the composition further comprises an immunosuppressive agent to prevent rejection of cells and/or treatment failure. This may be especially useful in case allogenic integrin alpha 10-selected MSCs alone or together with allogenic keratinocytes are in the composition of the present disclosure.

Methods and Uses

One aspect of the present disclosure provides a use of a composition comprising an integrin alpha 10-selected MSCs, for the preparation of a medicament for the treatment of a skin defect.

Another aspect of the present disclosure provides a method of treating a skin defect in a mammal in need thereof comprising administering a composition comprising integrin alpha 10-selected MSC to the mammal in an amount effective to treat the skin defect.

One aspect of the present disclosure relates to a non-therapeutic cosmetic use of a composition comprising integrin alpha 10-selected Mesenchymal Stem Cells (MSCs) for reducing scar formation resulting from healing of a skin defect in a mammal.

In another aspect of the present disclosure it is provided a use of a composition comprising integrin alpha 10-selected Mesenchymal Stem Cells (MSCs) for non-therapeutic treatment of a skin defect in a mammal.

The composition comprising integrin alpha 10-selected MSCs of the present disclosure can be also used for reducing or minimizing scars, for example for reducing or minimizing scar formation. The terms "reducing or minimizing" as used herein, preferably, refer to the administration of the composition of the present disclosure to a subject in order to reduce or minimize de novo formation of scars. Moreover, the reduction of scars preferably, also, comprises the amelioration or prevention of pain and/or pruritus during scar formation. In order to reducing scars, the composition of the present disclosure is preferably, topically administered to the site of a skin defect while the skin defect is in the process of healing.

In some embodiments of the present disclosure, it is provided a cosmetic composition comprising integrin alpha 10-selected MSCs, wherein the composition further comprises a cosmetically acceptable carrier.

In some embodiments of the present disclosure, it is provided a non-therapeutic composition comprising integrin alpha 10-selected MSCs, wherein the composition further comprises a cosmetically acceptable carrier.

EXAMPLES

Example 1: Production of Integrin Alpha 10-Enriched MSCs

Aim

This example illustrates how integrin alpha 10-selected MSCs are isolated, selected, expanded and stored until usage in the treatment model.

The term "XSTEM" as used herein is synonymous to the term "integrin alpha 10-enriched MSCs", XSTEM is the internal designation used to refer to integrin alpha10-enriched MSC".

Material and Methods

Integrin alpha 10-selected mesenchymal stem cells (MSCs) were isolated from human or animal adipose donor tissue or from other MSC-containing sources. The adipose tissue was dissociated/digested and the adipose-derived stromal vascular fraction (SVF) was re-suspended in MSC expansion medium and seeded into cell culture flasks to allow the MSCs to adhere to the plastic and proliferate.

The plastic-adherent cells were analyzed for positive expression (≥95%) of the cell surface markers CD73, CD90 and CD105, and negative expression (≤2%) of CD45, CD34, CD11b, CD19 and HLA-DR, as measured by flow cytometry. This specific antigen expression criteria is also a part of the MSC definition set by the International Society for Cellular Therapy (Dominici 2006). The MSC-preparation was expanded in monolayer cultures in MSC expansion medium and integrin alpha 10-expressing MSCs were selected using antibodies specifically binding to integrin alpha 10 (thereby recognizing the full receptor integrin alpa10 beta1, i.e. integrin $\alpha10\beta1$) and magnetic bead separation or selected by FACS cell sorting. The integrin alpha 10-selected MSC were further expanded, checked for cell surface expression of the defined MSC antigens and in addition, trilineage differentiation capability was demonstrated. The alpha 10-selected MSCs were frozen live in cryopreservation medium and kept frozen until use.

Results

The procedure resulted in integrin alpha 10-selected MSCs (XSTEM), expanded and frozen in vials which can be used for administration, for example local administration.

Conclusions

The manufacturing process generates alpha 10-selected MSCs fulfilling the minimal criteria defining human MSCs and could be applied in cell therapy.

Example 2: Wound Healing Factors Secreted by Integrin Alpha 10-Selected MSCs

Aim

This example illustrates the paracrine effects of integrin alpha 10-enriched MSC (XSTEM) by secretion of immunomodulatory, anti-inflammatory and pro-regenerative factors. The term "XSTEM" as used herein is synonymous to the term "integrin alpha 10-enriched MSCs".

Material and Methods

Integrin alpha 10-selected mesenchymal stem cells (XSTEM) were stimulated with the pro-inflammatory cytokines interferon gamma (IFNγ) and tumour necrosis factor alpha (TNFα) for 72 hours. The conditioned medium was collected and analysed by enzyme-linked immunosorbent assay (ELISA) for indoleamine 2,3-dioxygenase (IDO) and prostaglandin E2 (PGE2). Concentration of vascular endothelial growth factor (VEGF) and hepatocyte growth factor (HGF) in the conditioned medium released by different cell number of XSTEM at steady state were also measured by Luminex multiplex assay.

Results

Figure 5:
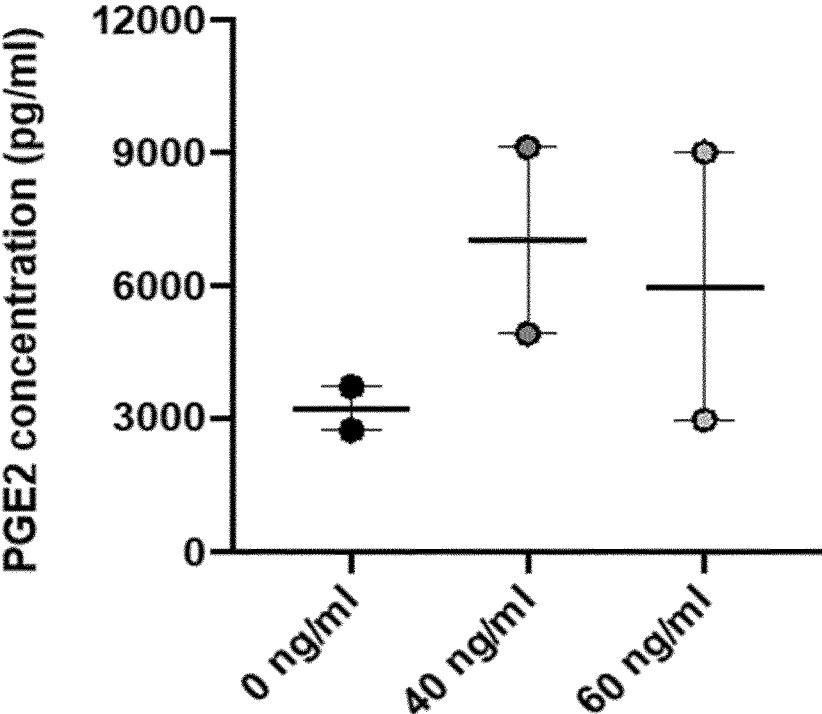
FIG. 5: Secretion of factors that promote wound healing. The concentration of secreted PGE2 (A) and IDO (B) was measured 72 hours after stimulating XSTEM with different concentrations of the pro-inflammatory cytokines IFNγ and TNFα (40 ng/mL and 60 ng/mL of each cytokine, respectively). Unstimulated (0 ng/mL) XSTEM served as a control. The concentration of secreted VEGF (C) and HGF (D) from XSTEM in conditioned medium is higher for cell preparations comprising a higher number of cells.
Figure 5:
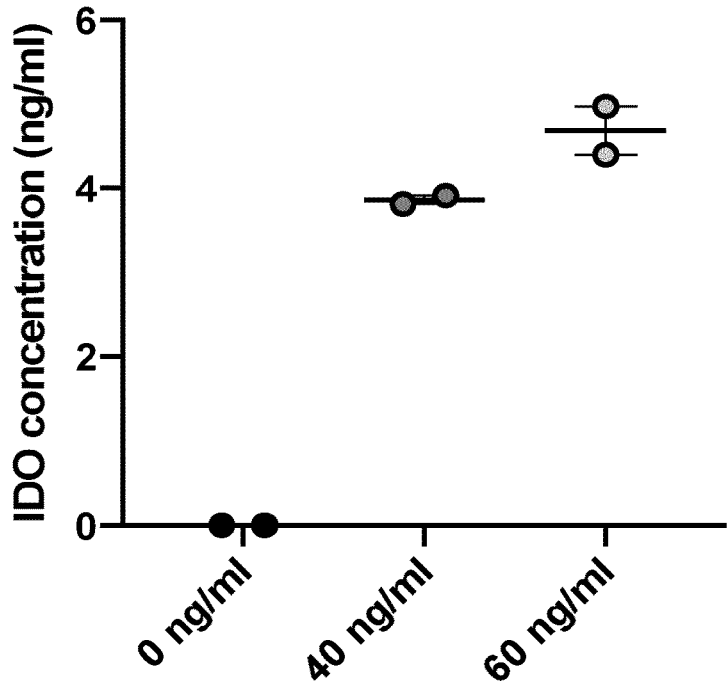

PGE2 was significantly expressed in the unstimulated XSTEM and the expression was further increased upon stimulation with IFNγ and TNFα (FIG. 5A). IFNγ and TNFα stimulation of XSTEM also induced expression of IDO (FIG. 5B). PGE2 and IDO are anti-inflammatory molecules known to have immunomodulatory roles by suppressing T-cell proliferation and promoting M2 polarisation of macrophages. In addition, XSTEM also secretes pro-regenerative growth factors including HGF and VEGF (FIG. 5C), which are known to promote skin wound healing (Guillamat-Prats et al. 2021). Based on previous studies showing that integrin alpha 10-selected MSCs secrete significantly more PGE2 that unselected MSCs (Uvebrant et al. 2019), it is expected that also the secretion of other anti-inflammatory and immunomodulatory factors such as IDO, HGF and VEGF is superior in integrin alpha 10-selected MSCs (and composition comprising a majority of these MSCs) compared to MSCs which have not been selected for integrin alpha 10 expression.

Conclusions

Integrin alpha 10-selected MSCs secretes key cytokines and growth factors that are known to promote wound healing process and tissue regeneration. Thus, integrin alpha 10-selected MSCs can successfully be used for treatment of skin defects including chronic or hard to heal wounds, such as wounds which are characterised by inflammation, thanks to their superior capability to secrete factors that promote wound healing, as well to the fact that they can regenerate skin, as demonstrate in Example 3.

Example 3: In Vivo Treatment of a Skin Defect

Aim

The aim of these experiments was to demonstrate and evaluate the therapeutic effect of the integrin alpha 10-selected MSCs for healing of a skin defect in a validated porcine model. Porcine skin approximates human skin in terms of skin attachment, hair coat, thickness of epidermis and dermis, and healing mechanism. Therefore, the pig is considered to be a relevant species for wound healing studies (Sullivan et al. 2001). In addition, the size and depth of full thickness wounds created in our study mimics chronic wounds as the large wound sizes did not allow spontaneous healing via contracture (Jeschke et al. 2017). The healing mechanism of chronic wounds is in principle the same as that of non-chronic wounds. However, chronic wounds are often hard to heal because inflammation and/or infection at the wound site, or presence of underlying diseases.

Material and Methods

A skin wound in-vivo study was conducted on two pigs according to the following workflow:
    On day 0, a full thickness biopsy of skin with underlying fat was surgically removed. The subcutaneous fat layer was mechanically dissociated. The fat portion was minced and incubated with shaking in collagenase I for 90 minutes at 37° C. in order to isolate adipose derived stem cells (ADSCs). The skin portion were cut into small pieces and incubated in dispase overnight at 4° C. Then the epidermis was mechanically peeled from the dermis and incubated with trypsin for 30 min at 37° C. After appropriate washes with phosphate buffered saline, the cells were counted and resuspended in 2.5% human serum albumin (clinical grade) in saline. The volume was adjusted to 1 ml for each group according to the target cell number.

On the following day (day 1), six critical size (at least an area of 3*3 cm) full thickness skin wounds were created surgically on the back of each pig.

Also on day 1, the isolated autologous cells as well as integrin alpha 10-selected MSCs, prepared as described in Example 1, were applied at different concentrations: autologous keratinocytes ($7\times10^5$ cells/wound); autologous stem cells (adipose derived stem cells (ADSCs), $5\times10^5$ cells/wound); integrin alpha 10-selected MSCs ($5\times10^5$ cells/wound); integrin alpha 10-selected MSCs+autologous keratinocytes ($5\times10^5+5\times10^5$ cells each/wound); integrin alpha 10-selected MSCs ($1\times10^6$ cells/wound) in wounds. The wounds were properly covered according to the surgical guidelines, and the cells were injected in the wound after applying the non-absorptive dressing.

Day 7: Healing (wound size and epithelization) of the skin defects was followed up after one week.

Day 14: Healing (wound size and epithelization) of the skin defects was followed up after two weeks. Moreover, the experiment was terminated and the wounds were excised for histological evaluation. The wounds were clinically evaluated and biopsies were collected, fixed and prepared for histological evaluation. The sections were stained with hematoxylin and eosin and Masson's trichrome stain according to the local protocols.

Results

Autologous ADSC and keratinocytes as well as human Integrin alpha 10-selected MSCs (XSTEM) were applied to full thickness, critical size skin wound model and followed up for two weeks. The cells were applied as $5\times10^5$ XSTEM cells with and without $5\times10^5$ autologous keratinocytes and $1\times10^6$ XSTEM cells. For control, $5\times10^5$ autologous ADSC, $7\times10^5$ autologous keratinocytes and vehicle were applied.

Macroscopically, no signs of inflammation, laceration or infection could be detected at any of the wounds (FIG. 1).

Figure 2:
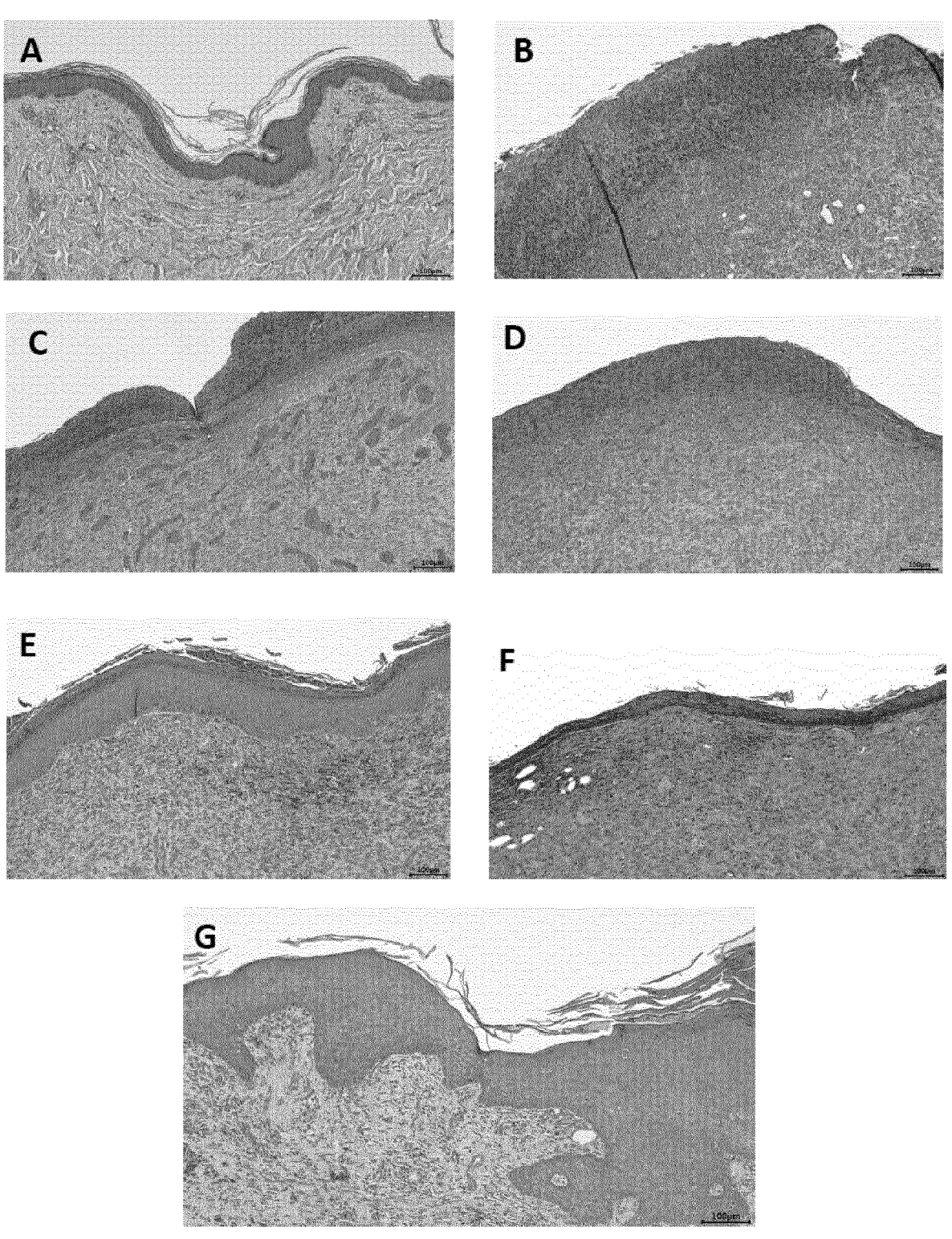
FIG. 2: Haematoxylin and Eosin staining for skin wound biopsies after two weeks of cell application. The epidermal architecture of XSTEM half a million cells (E) was comparable to the normal skin biopsy (A), while the epidermal thickness was less when the cells were combined with autologous keratinocytes (F). XSTEM one million cells were associated with less organized epidermis and hyperkeratosis (G). The epidermal development was less efficient with autologous half a million stem cells (D), autologous $7 \times 10^5$ keratinocytes (C) and the vehicle (B). The Scale bar was set at 100 μm.

Haematoxylin and Eosin staining showed that the epidermal architecture of XSTEM half a million cells was comparable to normal skin (FIGS. 2E and A). The epidermal thickness was less when the cells were combined with autologous keratinocytes (FIG. 2F). XSTEM one million cells were associated with less organized epidermis and hyperkeratosis (FIG. 2G). The epidermal development was less efficient with autologous stem cells, keratinocytes or the vehicle (FIG. 2D, C, B, respectively).

Figure 3:
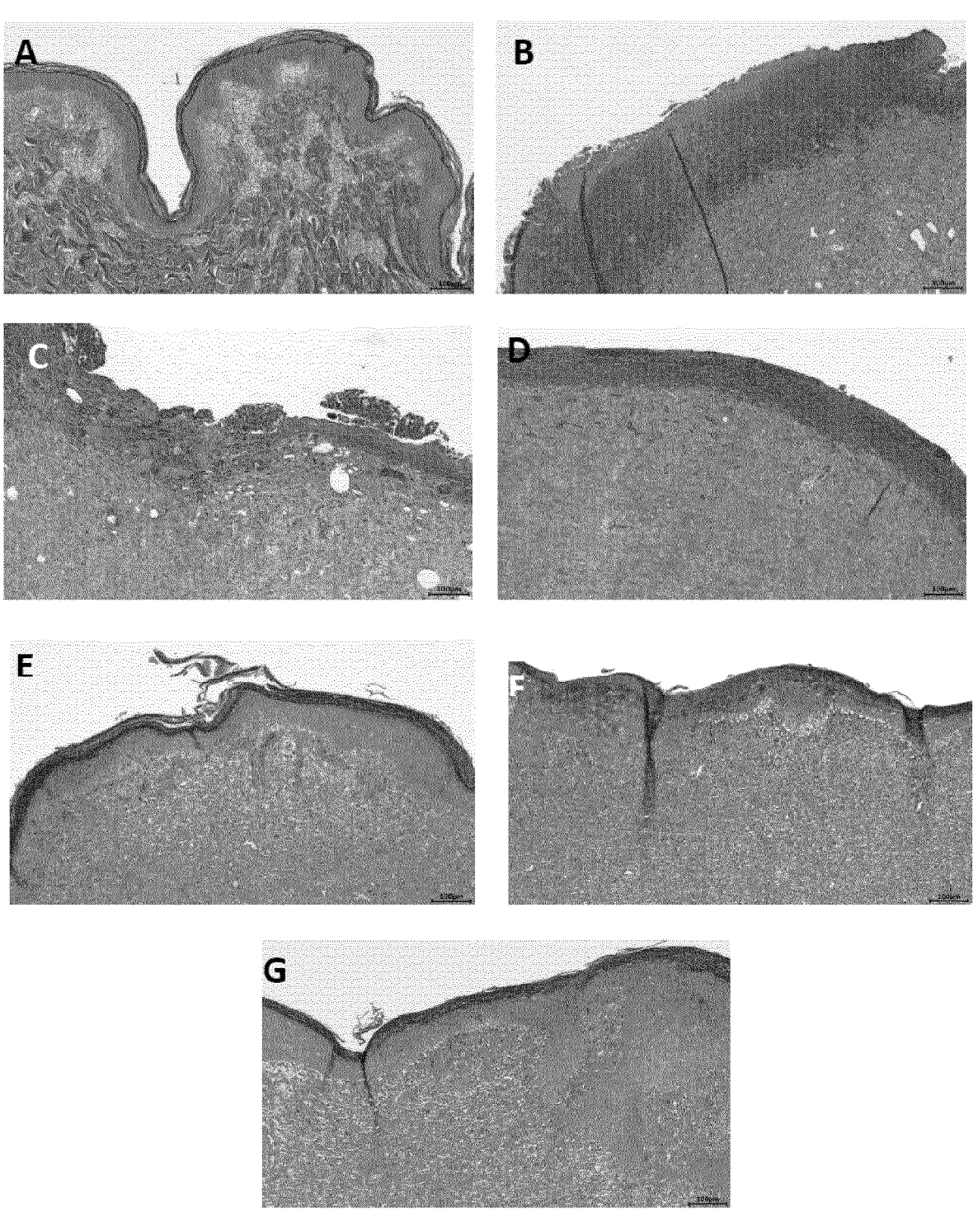
FIG. 3: Masson trichrome staining for skin wound biopsies after two weeks of cell application. The collagen fascicular pattern and intensity of staining for XSTEM half a million cells (E) was comparable to the normal skin biopsy (A). The intensity of collagen staining was higher than the control when the cells were combined with autologous keratinocytes (F) or with autologous half a million stem cells (D). XSTEM one million cells were associated with less organized epidermis and less intense collagen staining (G), while the autologous $7 \times 10^5$ keratinocytes (C) was associated with less collagen production in comparison to the vehicle (B). The Scale bar was set at 100 μm.
Figure 4:
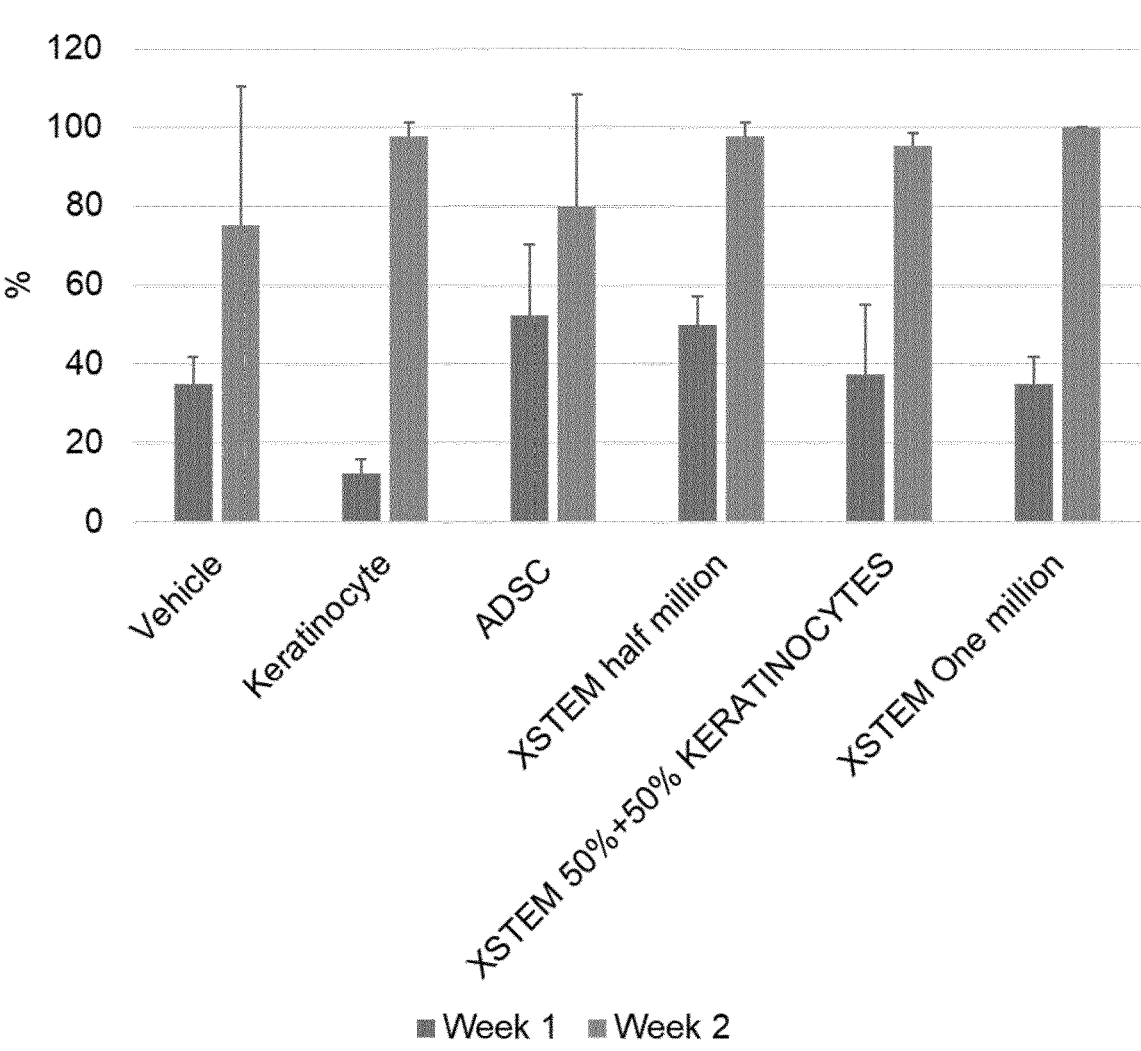
FIG. 4: Clinical evaluation of epithelization (A) and wound size (B). XSTEM half million cells showed a trend of better epithelization in comparison to the vehicle after one week and two weeks, which reflects quicker healing of the wound. Furthermore, XSTEM half million cells had better epithelization trend than most of the studied groups, especially at the early time point (7 days). The change of wound size, which happens mainly by wound edge contraction did not seem to be affected by any of the studied cell types.

Masson trichrome staining showed that the collagen fascicular pattern and intensity of staining for XSTEM half a million cells was comparable with normal skin (FIGS. 3E and A). The intensity of collagen staining was higher than the control when the cells were combined with autologous keratinocytes or with autologous stem cells (FIGS. 3F and D). XSTEM one million cells were associated with less organized epidermis and less intense collagen staining (FIG. 3G), while autologous keratinocytes were associated with less collagen production in comparison to the vehicle (FIGS. 3C and B).

Conclusions

Local treatment of a skin defect $5\times10^5$ (half million) integrin alpha 10-selected MSCs/wound resulted in regeneration of basal membrane, keratinization of the skin and formation of high level of collagen structured in bundles and resembling the naturally occurring collagen in skin, after 14 days. Regeneration of dermis and epidermis was observed also for local treatment with 1 million integrin alpha 10-selected MSCs/wound, although less organized epidermis was observed. None of these effects could be observed in skin defects treated with vehicle (placebo), autologous stem cells, or autologous keratinocytes.

REFERENCES

Hady Shahin, Moustafa Elmasry, Ingrid Steinvall, Katrin Markland, Pontus Blomberg, Folke Sjoberg, Ahmed El-Serafi (2020). Human Serum Albumin as a Clinically Accepted Cell Carrier Solution for Skin Regenerative Application. Scientific Reports 10:14486.

Matilda Karlsson, Ingrid Steinvall, Pia Olofsson, Johan Thorfinn, Folke Sjöberg, Liselott Åstrand, Fayiz S., Ahmad Khalaf, Divyasree Parambath, Ahmed T. El-Serafi, Moustafa Elmasry (2020). Sprayed Cultured Autologous Keratinocytes in the Treatment of Severe Burns: A Retrospective Matched Cohort Study. Annals of Burns and Fire Disasters 33:134-142.

Anjali Raghuram, Roy Yu, Andrea Lo, Cynthia Sung, Melissa Bircan, Holly Thompson, Alex K Wong (2020). Role of stem cell therapies in treating chronic wounds: A systematic review. World Journal of Stem Cells 12, 659-675.

Nina Kosaric, Harriet Kiwanuka and Geoffrey C Gurtner (2019) Stem cell therapies for wound healing. Expert Opinion on Biological Therapy 19: 575-585.

Ahmed T El-Serafi, Moustafa Elmasry and Folke Sjöberg (2018). Cell Therapy, the Future Trend for Burn Management. Editorial in Clinics in Surgery 3:1896.

Ahmed T. El-Serafi, Ibrahim El-Serafi, Moustafa Elmasry, Ingrid Steinvall, Folke Sjöberg (2017). Skin Regeneration in Three Dimensions, Current Status, Challenges and Opportunities. Differentiation 96: 26-29.

Dominici M et al., Cytotherapy. 8(4):315-7 (2006)

Garcia-Bernal, D., et al., The Current Status of Mesenchymal Stromal Cells: Controversies, Unresolved Issues and Some Promising Solutions to Improve Their Therapeutic Efficacy. Front Cell Dev Biol, 2021. 9: p. 650664.

Uvebrant K., Reimer Rasmusson L., Talts J F., Alberton P., Aszodi A. and Lundgren-Åkerlund E. "Integrinα10β1-selected Equine MSCs have Improved Chondrogenic Differentiation, Immunomodulatory and Cartilage Adhesion Capacity." Ann Stem Cell Res. 2,001-009 (2019). Sullivan T P, Eaglstein W H, Davis S C, Mertz β. The pig as a model for human wound healing. Wound Repair Regen. 2001 March-April; 9(2):66-76.

Jeschke M G, Sadri A R, Belo C, Amini-Nik S. A surgical device to study the efficacy of bioengineered skin substitutes in mice wound healing models. Tissue Eng Part C Methods. 2017; 23:237-4

Guillamat-Prats, R., The Role of MSC in Wound Healing, Scarring and Regeneration. Cells, 2021. 10(7)

The invention claimed is:

1. A method for treatment and/or regeneration of a skin defect, comprising administering a therapeutically effective amount of a composition comprising integrin alpha10-selected Mesenchymal Stem Cells (MSCs) to a subject in need thereof, wherein at least 60% of the MSCs express integrin alpha10 subunit.

2. A method for prevention of fibrosis of the skin comprising administering a therapeutically effective amount of a composition comprising integrin alpha10-selected Mesenchymal Stem Cells (MSCs) to a subject in need thereof.

3. A method for regeneration of skin at the site of a skin defect and/or for reducing scar formation resulting from healing of a skin defect comprising administering a composition comprising integrin alpha10-selected Mesenchymal Stem Cells (MSCs) to a subject in need thereof.

4. The method according to claim 1, wherein the skin defect is a hard-to-heal wound.

5. The method according to claim 4, wherein the hard-to-heal wound is a chronic wound.

6. The method according to claim 4, wherein the hard-to-heal wound is associated with venous insufficiency, arterial insufficiency and diabetic complications, a rare disease, or is a pressure-related hard-to-heal wound.

7. The method according to claim 4, wherein the hard-to-heal wound is a dermal ulcer, a wound, or a skin defect due to vascular insufficiency or diabetic affection of the blood vessels.

8. The method according to claim 1, wherein the skin defect is a skin disorder provoked by external factors, an inflammatory dermatosis, a postprocedural disorder of the skin, or a genetic and/or developmental disorder affecting the skin.

9. The method according to claim 8, wherein the skin disorder provoked by external factors is selected from a pressure ulceration, dermatoses provoked by friction or mechanical stress, dermatoses due to foreign bodies, dermatoses provoked or exacerbated by exposure to cold, dermatoses provoked by heat or electricity, dermatoses provoked by light or UV radiation, dermatoses due to ionizing radiation, allergic contact dermatitis, photo-allergic contact dermatitis, irritant contact dermatitis, allergic contact urticarial, protein contact dermatitis, allergic contact sensitization, phototoxic reactions to skin contact with photoactive agents, cutaneous reactions to venomous or noxious animals, a burn, a pressure sore from extended bed rest, a skin defect induced by trauma, and a cut.

10. The method according to claim 8, wherein the inflammatory dermatosis is selected from a dermatitis, eczema, atopic dermatitis, papulosquamous dermatoses, urticaria, angioedema or other urticarial disorders, inflammatory erythemas and other reactive inflammatory dermatoses, immunobullous diseases of the skin, cutaneous lupus erythematosus, and scarring or sclerosing inflammatory dermatoses.

11. The method according to claim 8, wherein the postprocedural disorder of the skin is an unsatisfactory surgical scar of skin, a cutaneous flap necrosis, a myocutaneous flap necrosis, a skin graft failure, a composite graft failure, or a surgical incision.

12. The method according to claim 8, wherein the genetic and/or developmental disorder affecting the skin is epidermolysis bullosa or genodermatosis.

13. The method according to claim 1, wherein the composition is administered topically to the skin defect, via injection, or a combination thereof.

14. The method according to claim 1, wherein the composition is dosed to comprise between 20.000 and 150.000 MSCs/cm$^2$ of skin defect to be treated.

15. The method according to claim 1, wherein the composition is administered in the form of a cell suspension in a pharmaceutically acceptable liquid medium.

16. The method according to claim 1, wherein the composition is administered on a dressing or reservoir.

17. The method according to claim 1, wherein the MSCs are MHCII negative, CD45 negative, CD34 negative, CD11b negative, CD19 negative and/or CD79 alpha negative; and/or wherein the MSCs express CD73, CD90 and/or CD105.

18. The method according to claim 1, wherein the MSCs are an in vitro cell suspension.

19. The method according to claim 1, wherein the MSCs have been selected by their expression of integrin alpha10 with an anti-integrin alpha10 antibody.

20. The method according to claim 1, wherein the MSCs are allogeneic or autologous.

* * * * *